United States Patent [19]
Hakac

[11] Patent Number: 6,102,849
[45] Date of Patent: Aug. 15, 2000

[54] NON-SURGICAL PENILE PROSTHESIS

[76] Inventor: John R. Hakac, 8626 E. Whitton Ave., Scottsdale, Ariz. 85251

[21] Appl. No.: 09/285,623

[22] Filed: Apr. 3, 1999

[51] Int. Cl.$^7$ ....................................................... A61F 5/00
[52] U.S. Cl. ................................................................ 600/39
[58] Field of Search ................................... 600/38, 39, 29

[56] References Cited

U.S. PATENT DOCUMENTS

| | | | |
|---|---|---|---|
| 3,446,206 | 5/1969 | De Lano | 600/39 |
| 4,869,241 | 9/1989 | Friedmann | 600/39 |
| 5,246,015 | 9/1993 | Baber | 600/40 |
| 5,336,157 | 8/1994 | Hale | 600/41 |

*Primary Examiner*—Max Hindenburg
*Assistant Examiner*—Brian Szmal

*Attorney, Agent, or Firm*—John D. Lister

[57] ABSTRACT

A 1-piece, non-surgical penile prosthesis (FIG. 1) molded of a biocompatible plastic comprising a specially designed, semi-rigid, rounded oblong tip (8) for retention in the fossa navicularis; a semi-rigid, narrow neck (10); a semi-rigid body (12); a semi-rigid taper (14); and a flexible tail (16, 18). The prosthesis (FIG. 1) is lightly lubricated for complete insertion into the male urethra. It is designed to aid males suffering from the common forms of erectile dysfunction. In use, the prosthesis (FIG. 1) is completely invisible and penetration is immediately possible. It comes with a 1-piece, semi-rigid practice device (FIG. 3) made of biocompatible plastic, which practice device is used for the training of male meatal dilation preparatory to using the prosthesis (FIG. 1). The practice device (FIG. 3) also provides the user with the preliminary experience of lubrication, insertion, removal, and the acquisition of skill and confidence in the form and use of the prosthesis (FIG. 1).

20 Claims, 1 Drawing Sheet

U.S. Patent  Aug. 15, 2000  6,102,849
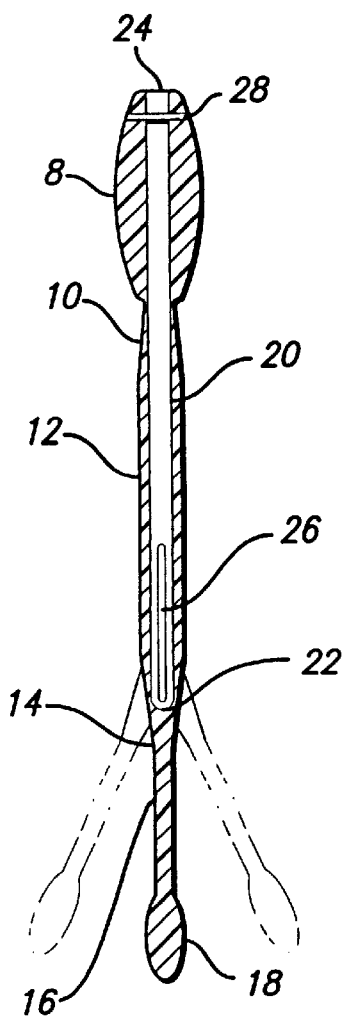
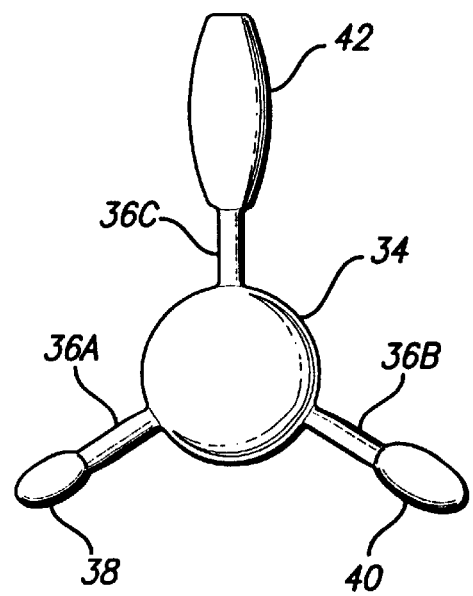
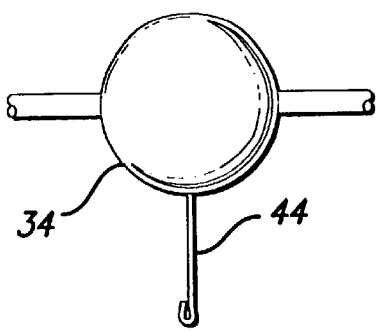
FIG. 1  FIG. 2  FIG. 3  FIG. 4  FIG. 5

NON-SURGICAL PENILE PROSTHESIS

BACKGROUND

1. Field of Invention

This invention relates to devices which provide non-surgical aid to help males with erectile dysfunction accomplish sexual intercourse.

2. Description of Prior Art

Prior art reveals numerous and highly varied attempts to equip men with erectile dysfunction for overcoming their inability to achieve and maintain a satisfactory erection necessary for completion of coitis. U.S. Pat. Nos. 3,446,206, 4,869,241, 5,246,015, and 5,336,157 illustrate the wide variety of such inventions. Their wide variety also seems to imply how difficult it has been to produce one practical, non-surgical invention with something resembling common acceptance because of its easy application and comfortable, gratifying success for both partners during sexual intercourse.

U.S. Pat. Nos. 5,246,015 and 5,336,157 are two different types of clamps designed to be visibly worn over the base of the penis for exerting pressure on penile veins, thus limiting the outflow of blood in order to create and maintain an erection.

U.S. Pat. No. 5,246,015 prevents venous leakage when wearing on the base of the penis a short, snugly fitting, external tube which acts to stimulate an erection when the proximal end of the tube touches the cruer of the penis. Presumably penile blood flow is normal and the rigid tube controls blood outflow by venous compression at the base of the penis as the penis becomes erect.

U.S. Pat. No. 5,336,157 is an adjustable clamp of two hinged rods or "legs" which visibly straddle the base of the penis. Elastic bands wound around a bendable hinge are used to compress and control pressure on both sides of an erect penis, thus retarding venous outflow of blood.

U.S. Pat. No. 3,446,206 is a complicated splint when compared to clamps, having external as well as internal (urethral) components. A support ring at the base of the penis, a penile-length rod which runs underneath the length of the penis, and a rubber-band loop, attached to the rod and looped over the glans penis are parts worn externally on the penis during intercourse. It is a highly visible splint which no doubt clouds the pleasurable act of sexual intercourse by its obvious reminder of necessary therapy.

U.S. Pat. No. 4,869,241 is a penile-length splint in the form of a hollow tube open at both ends for the passage of body fluid and made to be kept partly in the male urethra. The tube's depth of insertion is limited by a plastic cap which fits over the face of the glans penis and is affixed permanently to the distal end of the tube. When used, the tube is inserted into the urethra until stopped by the plastic cap. A condom-like sleeve attached to the rim of the plastic cap is then unrolled over the penis as one would unroll a condom. Another embodiment would rely on an off-the-shelf condom to hold the inserted splint in place. Although seemingly practical and promising in its simplicity, the splint has the serious flaw of significantly covering the face of the glans penis, the most sensitive part of male sexual anatomy. A more serious problem inherent in this splint is its lack of a reliable, secure "lock-in" feature. The invention relies on a plastic cap to keep the semi-rigid splint from entering the urethra too deeply, but it clearly lacks a safe, dependable means to insure that the splint does not protrude from the urethra while in use and thus cause at least alarm and possibly injury to one or both partners. Relying on a condom-like sleeve or an off-the-shelf condom to prevent the splint's emergence during intercourse would be extremely risky. Condoms have been known to break, to slip, and even to slip off during intercourse.

The patents briefly summarized illustrate typical features of non-surgical aids for erectile dysfunction. They clearly interfere with the normal pleasure of intercourse by shortening penile length or significantly desensitizing sexual activity. Male pride and pleasure in making love are closely tied to penile length and the keen sensation of tactile excitement. Although common clamps and splints may be partly effective in enabling some men with erectile dysfunction to attempt normal sexual activity, their unfortunate designs which shorten penile length, their external locations on male anatomy, and their obvious visibility and tactile discomfort cannot but diminish the pride and gratification of sexual fulfillment for both partners. In addition, conspicuous appliances are known to make a woman partner somewhat less than happy because a female partner likes to believe that she is herself appealing enough for male sexual responses. External appliances or parts of appliances can easily be a "turn-off" by making a woman partner feel inadequate.

Since the 1970's there has been an accelerated pace to solve the problems of erectile dysfunction: clasps, splints, vacuum pumps with constriction rings, expensive surgical implants of many designs, pharmacological injections, urethral pellets, and most recently an oral pill containing sildenafil. Side-effects, mechanical failures, injuries, serious infections, irreversible procedures, corrective surgery, and frequently costs in the thousands of dollars are examples of the many difficulties associated with these attempts to restore sexual activity for males suffering with erectile dysfunction.

When one considers the limitless variations of human behavior during sexual intercourse, from adolescence to superannuation, and in various conditions of sobriety to all types of altered consciousness, available non-surgical aids for erectile dysfunction are very cumbersome, psychologically distracting, uncomfortably impractical, and possibly injurious. There is, clearly, a pressing need for a greatly improved non-surgical penile prosthesis. Such an invention should be quickly inserted and removed, completely invisible, and in no tactile way an interference with the psychological and physical pleasure of a joyful and fulfilling sexual experience for both partners, one which is always free of delay, free of failure, and free of side-effects and injuries.

SUMMARY OF INVENTION

The present invention is a simple, 1-piece, non-surgical penile prosthesis in the form of a urethral insert molded of biocompatible plastic. It is designed for males suffering from the common types of erectile dysfunction: inability to have an erection, slowness in achieving an erection, and failure to maintain an erection for completion of sexual intercourse. The prosthesis comes with a practice device for meatal dilation training which provides the user with a preliminary experience of lubrication, insertion, removal, and the acquisition of skill and confidence in the device's form and use. When the prosthesis is inserted, penetration is immediately possible even if the penis temporarily lacks the full qualities of a normal erection.

DRAWING FIGURES

FIG. 1 is a sectional view of the prosthesis showing all its parts.

FIG. 2 is a top view of the open-ended oblong tip showing the exit port for body fluid and the access port for the stainless steel extractor pin.

FIG. 3 is a top view of the practice device showing the ball handle, the three oblong tips (small, medium, large), the large oblong tip being equal in length and girth to the oblong tip of the prosthesis.

FIG. 4 is a partial side view of the practice device showing the stainless steel extractor affixed to the ball handle.

FIG. 5 is a side view of an embodiment of the prosthesis for use by males who have retrograde ejaculation.

REFERENCE NUMERALS IN DRAWINGS

| | |
|---|---|
| 8 rounded oblong tip | 30 top view of oblong tip |
| 10 narrow neck | 32 access port to extractor pin |
| 12 body | 34 ball handle |
| 14 taper | 36A extender rod |
| 16 flexible tail | 36B extender rod |
| 18 bulb of tail | 36C extender rod |
| 20 hollow tube | 38 small tip |
| 22 closed end of tube | 40 medium tip |
| 24 open end of tube | 42 large tip |
| 26 longitudinal slits | 44 extractor |
| 28 extractor pin | |

DETAILED DESCRIPTION OF THE INVENTION

The present invention is a 1-piece penile prosthesis FIG. 1 molded of a biocompatible plastic and designed for complete insertion into the male urethra. It is essentially a semi-rigid body 12 with a hollow tube 20, open at the distal end 24 and closed at the proximal end 22 of a taper 14, comprising a semi-rigid round oblong tip 8; a transverse stainless steel extractor pin 28; a semi-rigid narrow neck 10; a semi-rigid body 12; a semi-rigid taper 14, which narrows to become an extended but solid and flexible tail 16 terminating with a round oblong bulb 18 slightly wider than the diameter of the tail 16; and a multiplicity of longitudinal slits 26 running from the lower end of the taper 14 for 2.5 cm to 4 cm or more up on the body 12. Three or more longitudinal slits 26, each slit evenly spaced radially, give the prosthesis FIG. 1 the capacity to eliminate body fluid which enters the prosthesis FIG. 1 through the longitudinal slits 26 and exits it through the open-ended tube 24. The semi-rigid body 12, longest part of the prosthesis FIG. 1, is of a diameter to fill the urethral canal without dilation, thus increasing the efficiency of the longitudinal slits 26 to eliminate body fluid. Stabilized polyethylene has desirable qualities for the semi-rigid oblong tip 8, the semi-rigid narrow neck 10, the semi-rigid body 12, and the semi-rigid taper 14. Vinyl has desirable qualities for the flexible tail 16 and its oblong bulb 18.

A 3-tipped practice device FIG. 3 is supplied with the prosthesis FIG. 1 because the meatus urinarius of the male penis must be trained to dilate before the prosthesis FIG. 1 can be inserted. The practice device FIG. 3 is also a 1-piece device molded of a semi-rigid biocompatible plastic. The three round oblong tips 38, 40, 42 of the practice device FIG. 3, mounted on short extender rods 36A, 36B, 36C which radiate on a flat plane equally distant from each other on a ball handle 34, are progressively larger—from small 38, to medium 40, to large 42. The large oblong tip 42 is equal in length and girth to the oblong tip 8 of the prosthesis FIG. 1. Affixed to the ball handle 34, perpendicularly to the plane of the extender rods 36A, 36B, 36C is a stainless steel extractor 44 which is described below.

The principal function of the practice device FIG. 3 is to train the meatus to dilate for passage of the oblong tip 8 of the prosthesis FIG. 1 through the meatus into the fossa navicularis, an enlarged urethral cavity in the glans penis. It is the unique ability of the meatus to dilate under pressure and quickly return to normal size and appearance which makes possible the secure and invisible retention of the oblong tip 8 in the fossa navicularis, thus keeping the entire prosthesis completely invisible and securely in place during use.

The first stage of meatal dilation training begins with coating the small oblong tip 38 of the practice device FIG. 3 with a thick lubricant having a consistency of petroleum jelly. With the thumb and index finger of the left hand placed as a loose ring-clamp behind the glans penis, the user, holding the ball handle 34, presses the lubricated small oblong tip 38 into the fossa navicularis. After a brief pause until some comfort is felt, the small oblong tip 38 is withdrawn using the ball handle 34. Pressure when the small oblong tip 38 is inserted and later withdrawn exercises meatal dilation. The process is repeated several times daily until it becomes easy to do and dilation becomes comfortable. Practicing a similar technique, the user progresses through stages two and three with the medium 40 and then the large 42 oblong tips of the practice device FIG. 3 until the user feels comfortable and has acquired confidence in the ability of the meatus to dilate as needed. When insertion and removal of the large oblong tip 42 of the practice device FIG. 3 have given the user skill and confidence with the procedure, he is prepared for insertion and removal of the prosthesis FIG. 1 itself.

Use of the prosthesis FIG. 1 after a period of meatal dilation training involves three steps also: lubrication, insertion, and removal. A thick lubricant with the consistency of petroleum jelly works very well. Picking up a small amount of lubricant on the tip of an index finger prepares the user for applying it lightly onto the prosthesis FIG. 1 with index finger and thumb, beginning at the bulbous end 18 of the tail 16 and working upward to the oblong tip 8. One or two applications of lubricant will suffice to coat the invention up to the oblong tip 8. The same method of index-finger-and thumb is used to coat the oblong tip 8. Once lubricated, the prosthesis FIG. 1 is easily slid tail first 18,16 through the meatus into the urethra until only the oblong tip 8 remains exposed. During insertion, the smooth movement of the flexible tail 16, 18 and the semi-rigid body 12 through the urethral canal provides a mild, pleasant thrill, a stimulation which helps to encourage erectile response. Additional tactile stimulation may be gained by increasing the length of the flexible tail 16, 18 to the neck of the bladder and even beyond.

To position the oblong tip 8 in the fossa navicularis, both hands are used. Thumb and index finger of the left hand form a ring-clamp held loosely behind the glans penis to hold it while pressing the oblong tip 8 through meatal dilation into the fossa navicularis with the tip of the thumb of the right hand. The dilated meatus very quickly returns to normal size and appearance. This technique is reversed for left-handed users. The oblong tip 8 is designed to stop the depth of insertion below the fossa navicularis as well as to keep the inserted prosthesis FIG. 1 securely locked in place during use.

Removal of the prosthesis FIG. 1 is accomplished with a stainless steel extractor 44. The extractor 44 is partially inserted into the open end 24 of the oblong tip 8, given a one-quarter turn to engage the stainless steel extractor pin 28, then pulled slowly and gently out of the fossa navicularis using the ball handle 34 of the practice device FIG. 3.

Lubrication, insertion, and removal of the prosthesis FIG. 1 become second-nature skills with practice. In normal use, lubrication and insertion are done in a minute or so, and removal with the stainless steel extractor 44 in much less than a minute. An alternative method of removal, perhaps preferred later by users who possess dexterity, employs thumb and index finger of both hands to press the oblong tip 8 out of the fossa navicularis. The specially designed narrow neck 10 of the Prosthesis FIG. 1 makes possible a larger underside of the oblong tip 8 on which to apply the force needed to press the oblong tip 8 out of the fossa navicularis. Again, the dilated meatus very quickly returns to normal size and appearance.

Medical texts on human anatomy use penile length to classify the male penis as small average, 11.5 cm (4½"); average, 15.3 cm (6"); and large average, 18 cm (7"). In accordance with medical research, the present invention is made in three sizes, with longer or shorter modifications of these sizes provided when appropriate. The flexible tail 16 and its terminal oblong bulb 18 increase the overall length of the prosthesis FIG. 1.

Some users of the invention will see and feel an enlargement of penile length and girth after a period of regular use. Because of the semi-rigid oblong tip 8, the semi-rigid narrow neck 10, the semi-rigid body 12, and the semi-rigid taper 14, the prosthesis FIG. 1 also has the ability to correct minor penile deformities.

Many men who have had prostate surgery discover that surgery has left them with retrograde ejaculation. Another embodiment of this invention as seen in FIG. 5 eliminates both the longitudinal tube 20 (except for the shallow recess 32 which houses the extractor pin 28) and the longitudinal slits 26. In cases of retrograde ejaculation there is no need to eliminate body fluid.

The general appearance of the prosthesis FIG. 1 and the practice device FIG. 3 will be enhanced by the use of color, a powerful symbol of visual and emotional experience. Color possibilities for them—solid, two-toned, or multi-colored—are as numerous as the primary colors of the color spectrum and the tints from mixing them.

Cleaning the prosthesis FIG. 1 and the practice device FIG. 3 is easily done: warm water, soap, and a chenille stem are adequate for a thorough cleansing.

Although the description above contains many specifications, these should not be taken as limiting the scope of the invention but merely providing illustrations of the presently preferred embodiments of this invention. Thus the scope of the invention should be determined by the appended claims and their legal equivalents rather than by the descriptions given herein.

I claim:

1. A non-surgical penile prosthesis for correcting erectile dysfunction in males, comprising:
    a urethral insert; the urethral insert having a distal end and an inner end; the distal end having an extractor means for use in extracting the urethral insert from a penis; the urethral insert having a semi-rigid oblong distal end portion with a generally round transverse cross section; the urethral insert having a semi-rigid neck portion, axially aligned with, extending inwardly from and integral with the distal end portion; the neck portion having a transverse cross section less than the transverse cross section of the distal end portion; the urethral insert having a semi-rigid body portion, axially aligned with, extending inwardly from and integral with the neck portion; the body portion having a transverse cross section greater than the transverse cross section of the neck portion; the urethral insert having a semi-rigid tapered portion, axially aligned with, extending inwardly from and integral with the body portion; the tapered portion having a transverse cross section which, from the body portion inward, is progressively less in cross section than the transverse cross section of the body portion; and the urethral insert having a flexible tail portion axially aligned with, extending inwardly from and integral with the tapered portion; the flexible tail portion terminating in a oblong bulbous portion greater in cross section than a remainder of the tail portion.

2. The non-surgical penile prosthesis for correcting erectile dysfunction in males, according to claim 1 wherein:
    the oblong distal end portion of the urethral insert has an opening therein at the distal end of the urethral insert; and the opening has a transverse extractor pin therein adjacent the distal end of the urethral insert for use in extracting the urethral insert from a penis.

3. The non-surgical penile prosthesis for correcting erectile dysfunction in males, according to claim 2 wherein:
    the oblong distal end portion, the neck portion, the body portion and at least part of the tapered portion are tubular; and there is opening means in the tapered portion for fluids to pass from outside the urethral insert into a tubular cavity formed by the tubular oblong end portion, the tubular neck portion, the tubular body portion and the tubular tapered portion of the urethral insert.

4. The non-surgical penile prosthesis for correcting erectile dysfunction in males, according to claim 3 wherein:
    the opening means comprises longitudinally extending slits passing radially from an exterior surface of the urethral insert to the tubular cavity and extending from within the tapered portion into the body portion.

5. The non-surgical penile prosthesis for correcting erectile dysfunction in males, according to claim 4 wherein:
    the slits extend for about 2.5 cm or more.

6. The non-surgical penile prosthesis for correcting erectile dysfunction in males, according to claim 5 wherein:
    the oblong distal end portion, the neck portion, the body portion and the tapered portion are made from a semi-rigid biocompatible plastic; and the tail portion is made from a flexible biocompatible plastic.

7. The non-surgical penile prosthesis for correcting erectile dysfunction in males, according to claim 1 wherein:
    the oblong distal end portion, the neck portion, the body portion and the tapered portion are made from a semi-rigid biocompatible plastic; and the tail portion is made from a flexible biocompatible plastic.

8. The non-surgical penile prosthesis for correcting erectile dysfunction in males, according to claim 1 wherein:
    the urethral insert is colored for sensual enhancement.

9. The non-surgical penile prosthesis for correcting erectile dysfunction in males, according to claim 1 wherein:
    the oblong distal end portion, the neck portion, the body portion and at least part of the tapered portion are tubular; and there is opening means in the tapered portion for fluids to pass from outside the urethral insert into a tubular cavity formed by the tubular oblong end portion, the tubular neck portion, the tubular body portion and the tubular tapered portion of the urethral insert.

10. The non-surgical penile prosthesis for correcting erectile dysfunction in males, according to claim 9 wherein:

the opening means comprises longitudinally extending slots passing radially from an exterior surface of the urethral insert to the tubular cavity and extending from within the tapered portion into the body portion.

11. The non-surgical penile prosthesis for correcting erectile dysfunction in males, according to claim 10 wherein:

the slots are evenly spaced with respect to each other and extend for at least 2.5 cm.

12. The non-surgical penile prosthesis for correcting erectile dysfunction in males, according to claim 1 wherein:

the neck portion, the body portion and the tapered portion are non-tubular.

13. The non-surgical penile prosthesis for correcting erectile dysfunction in males, according to claim 12 wherein:

the oblong distal end portion of the urethral insert has an opening therein at the distal end of the urethral insert; and the opening has a transverse extractor pin therein adjacent the distal end of the urethral insert for use in extracting the urethral insert from a penis.

14. The non-surgical penile prosthesis for correcting erectile dysfunction in males, according to claim 12 wherein:

the oblong distal end portion, the neck portion, the body portion and the tapered portion are made from a semi-rigid biocompatible plastic; and the tail portion is made from a flexible biocompatible plastic.

15. A non-surgical appliance combination for correcting erectile dysfunction in males, comprising:

a urethral insert; the urethral insert having a distal end and an inner end; the distal end having an extractor means for use in extracting the urethral insert from a penis; the urethral insert having a semi-rigid oblong distal end portion with a generally round transverse cross section; the urethral insert having a semi-rigid neck portion, axially aligned with, extending inwardly from and integral with the distal end portion; the neck portion having a transverse cross section less than the transverse cross section of the distal end portion; the urethral insert having a semi-rigid body portion, axially aligned with, extending inwardly from and integral with the neck portion; the body portion having a transverse cross section greater than the transverse cross section of the neck portion; the urethral insert having a semi-rigid tapered portion, axially aligned with, extending inwardly from and integral with the body portion; the tapered portion having a transverse cross section which, from the body portion inward, is progressively less in cross section than the transverse cross section of the body portion; and the urethral insert having a flexible tail portion axially aligned with, extending inwardly from and integral with the tapered portion; the flexible tail portion terminating in a oblong bulbous portion greater in cross section than a remainder of the tail portion; and a practice device for the training of male meatal dilation preparatory to using the urethral insert; the practice device including a ball handle for gripping with one hand; a first short extender rod extending radially outward from the ball handle; a free end of the first extender rod having an oblong tip with a generally circular cross section; a second short extender rod extending radially outward from the ball handle; a free end of the second extender rod having an oblong tip with a generally circular cross section; the oblong tip of the second extender rod being greater in cross section than the cross section of the oblong tip of the first extender rod; a third short extender rod extending radially outward from the ball handle; a free end of the third extender rod having an oblong tip with a generally circular cross section; the oblong tip of the third extender rod being greater in cross section than the cross section of the oblong tip of the second extender rod.

16. The non-surgical appliance combination for correcting erectile dysfunction in males, according to claim 15 wherein:

the oblong distal end portion of the urethral insert has an opening therein at the distal end of the urethral insert; and the opening has a transverse extractor pin therein adjacent the distal end of the urethral insert for use in extracting the urethral insert from a penis.

17. The non-surgical appliance combination for correcting erectile dysfunction in males, according to claim 16, wherein:

the practice device has an extractor means for cooperating with the transverse extractor pin of the urethral insert to remove the urethral insert from a penis.

18. The non-surgical appliance combination for correcting erectile dysfunction in males, according to claim 17 wherein:

the extractor means is a hook.

19. The non-surgical appliance combination for correcting erectile dysfunction in males, according to claim 15 wherein:

the oblong distal end portion, the neck portion, the body portion and the tapered portion of the urethral insert are made from a semi-rigid biocompatible plastic; the tail portion of the urethral insert is made from a flexible biocompatible plastic; and the practice device is made from a semi-rigid biocompatible plastic.

20. The non-surgical appliance combination for correcting erectile dysfunction in males, according to claim 15 wherein:

the urethral insert and the practice device are colored for sensual enhancement.

* * * * *

UNITED STATES PATENT AND TRADEMARK OFFICE
CERTIFICATE OF CORRECTION

PATENT NO. : 6102849
DATED : August 15, 2000
INVENTOR(S) : John R. Hakac

It is certified that error appears in the above-indentified patent and that said Letters Patent is hereby corrected as shown below:

Column 4, line 3, change "clasps" to ----- clamps ------.

Signed and Sealed this

Tenth Day of April, 2001

*Attest:*

NICHOLAS P. GODICI

*Attesting Officer*   *Acting Director of the United States Patent and Trademark Office*